United States Patent [19]

Homer et al.

[11] Patent Number: 4,809,190

[45] Date of Patent: Feb. 28, 1989

[54] CALORIMETRY SYSTEM

[75] Inventors: John C. Homer, Chardon; Shahriar Nowshiravani, Mayfield Heights; Steven L. Ross, Cleveland; Gilbert F. Lutz, Chesterland, all of Ohio

[73] Assignee: General Signal Corporation, Stamford, Conn.

[21] Appl. No.: 36,048

[22] Filed: Apr. 8, 1987

[51] Int. Cl.$^4$ .................................. G01L 3/26
[52] U.S. Cl. .................................. 364/510; 364/500; 364/172; 364/550; 374/36; 374/37; 374/8
[58] Field of Search ............... 364/500, 510, 550, 551, 364/172, 557; 374/36, 37, 43, 29, 8, 40, 41, 54; 110/185, 342

[56] References Cited

U.S. PATENT DOCUMENTS

| | | | |
|---|---|---|---|
| 1,869,585 | 8/1932 | Schmidt | 374/36 |
| 2,026,179 | 12/1935 | Keith | 374/36 |
| 3,988,926 | 11/1976 | Haas | 374/31 |
| 4,057,376 | 11/1977 | Matovich | 422/202 |
| 4,074,360 | 2/1978 | Stadie et al. | 364/551 |
| 4,108,301 | 8/1978 | Trozzi | 198/633 |
| 4,115,862 | 9/1978 | Stewart | 364/500 |
| 4,126,396 | 11/1978 | Hartmann | 356/434 |
| 4,156,590 | 5/1979 | Pariani | 431/3 |
| 4,324,495 | 4/1982 | Martinez | 198/498 |
| 4,345,463 | 8/1982 | Wilson | 374/36 |
| 4,353,427 | 10/1982 | Stock | 73/1 B |
| 4,386,858 | 6/1983 | Kude | 374/37 |
| 4,501,552 | 2/1985 | Wakamiya | 364/477 |
| 4,580,504 | 4/1986 | Beardmore | 110/261 |
| 4,580,698 | 4/1986 | Ladt | 198/505 |
| 4,595,125 | 6/1986 | Alwerud | 198/505 |
| 4,635,572 | 1/1987 | Nickel | 110/343 |

FOREIGN PATENT DOCUMENTS 2111708 9/1972 Fed. Rep. of Germany .

OTHER PUBLICATIONS

Fluid Data Inc., Bull. 20:F1-1, 9/84.

Primary Examiner—Parshotam S. Lall
Assistant Examiner—Ellis B. Ramirez
Attorney, Agent, or Firm—Martin Lukacher; J. S. Mednick

[57] ABSTRACT

A calorimetry systems for the continuous measurement of the heating value of coal, which provides heating value data used to control coal-fired furnaces. The system has apparatus for pulverizing the coal, a gravimetric feeder for providing pulverized coal at a measured mass feed rate, an initiating self-sustained combustion of the coal therein without the need for further supporting fuel gases. Instrumentation measures the flow rates of the cooling air, primary and secondary combustion air as well as the mass flow rates of the coal into the combustor. A computer is provided which is responsive to the measuring instruments (thermocouples and pressure gauges) for controlling the feeding of the coal and fuel gases during initiation of combustion and for computing the heating value of the coal. The computer has a memory with storage for specific heat values of the constituents of the products of combustion of various ranks of coal (bituminous, subbituminous, lignite, etc.) and the average mass fraction of each constituent in the coal by rank so that the heating value thereof can be determined with accuracy.

23 Claims, 6 Drawing Sheets

CALORIMETRY SYSTEM

DESCRIPTION

The present invention relates to calorimetry systems, and particularly to a calorimetry system for measuring the heating value or heat of combustion of solid fossil fuel, such as coal, continuously and directly so that the result may be used on-line in the control of processes in which the fuel is used.

The invention is especially suitable for use in coal-fired utility power plants for the on-line measurement of the heating value of the coal used to fire the furnaces in such plants. Aspects of the invention are also applicable in improving combustion calorimetry.

Heats of combustion of solid fuels such as coal are generally measured with a bomb calorimeter. Bomb calorimetry is an absolute and direct method of deriving heat by the combustion of a sample and applies the first law of thermodynamics to the original sample mass and temperature rise of calorimeter to calculate the heating value from the heat release per unit mass of the sample. Bomb calorimetry is still the state of the art for measuring the heating value of solid or liquid fuels. Such measurements must be made off-line and are not of the type which can be used to control continuous processes such as the control of steam generator firing systems in utility power generating plants.

Continuous flow calorimetry has long been used to measure the heat of combustion of gaseous fuel. See for example Sears and Zemansky, University Physics, Second Edition which was published first in the 1930's (Chapter 16-7). Such systems sometimes operate in accordance with the first law of thermodynamics by measuring the heat released from the gas by its effect on some other fluid system. Reference may be had to the following U.S. patents for further information to system for gas calorimetry of this type: U.S. Pat. Nos. to Schmidt, 1,869,585 issued Aug. 2, 1932; Keith, 2,026,179 issued Dec. 31, 1935; Pinkerton, 2,349,517 issued May 23, 1944; Toyoda et al., 3,472,071 issued Oct. 14, 1969; Grey, 3,665,763 issued May 30, 1972; and Calvet et al., 4,500,214 issued Feb. 19, 1985. Other calorimetry techniques do not involve absolute and direct measurements, but rely on the chemical and physical analysis of the gaseous fuel. Such indirect gaseous calorimetry techniques are mentioned in the following U.S. Pat Nos.: Haas, 3,988,926 issued Nov. 2, 1976; Stewart, 4,115,862 issued Sept. 19, 1978; Wilson et al., 4,345,463 issued Aug. 24, 1982; and Kude et al., 4,386,858 issued June 7, 1983. A commercial continuous flow gas calorimeter is described in Product Bulletin "Flo-Cal" TM High Speed Calorimeters Bulletin No. 20:FC-1 published by Fluid Data Incorporated, Merrick, N.Y., U.S.A. 11556 (the bulletin is dated 9-84).

Such gas calorimeters which rely upon combustion are adversely affected in their accuracy of measurement by heat loss. Errors due to heat loss must be calibrated out and are also highly dependent on ambient temperature and pressure.

The problem of accurate calorimetry of coal is exacerbated by the diverse chemical composition of the coal which affects the accurate consideration of the heat capacity of each component and its fractional mass in the total mass of the coal. The measurements are further made more difficult by heat loss as well as the destabilizing effects of changes in ambient temperature and pressure. Another problem with coal calorimetry is maintaining self-sustained combustion of the coal. This includes problems of feeding of the coal to the combustor both during start-up and continuous measurements in the calorimeter.

Accordingly, it is the principal object of the present invention to provide an improved calorimetry system which is especially adapted for measuring the heating value or heat of combustion of solid fuels, such as coal, on a direct and continuous basis so as to be suitable for use on-line in providing data for controlling industrial processes involving the combustion of the solid fuel, and particularly coal-fired steam generators of utility power plants.

It is another object of the present invention to provide an improved calorimetry system which operates under the first law of thermodynamics by combustion of the fuel whose heating value is to be determined and the mixing of the combustion gases with a cooling gas by the method of mixtures in which heat loss during combustion as well as during mixing is minimized so as to reduce unaccounted heat loss and stabilize against perturbations in ambient conditions.

It is a further object of the present invention to provide an improved method of calorimetry for coal or other solid fuel which derives heat from combustion of the fuel directly and continuously by self-sustained combustion thereof.

It is a still further object of the present invention to provide an improved continuous calorimetry system which relies upon the first law of thermodynamics, wherein the temperature rise of a cooling gas when combined with combustion gases is used, and in which the thermal capacity of the system is minimized so as to enable rapid response to changes in heating value of the material under test.

It is a still further object of the present invention to provide an improved continuous calorimetry system which provides absolute (non-inferential), direct measurements of heating value of solid fuel, such as coal, wherein the gravimetric feed rate of the fuel and the mass rate of flow of the resulting combustion gas formed upon combustion of the fuel, can be measured directly together with the increase in temperature of the cooling gas to determine the heating value of the fuel independently of variations in ambient pressure and temperature.

It is a still further object of the present invention to provide an improved system for continuous calorimetry of a supply of coal wherein self-sustained combustion of the coal occurs.

Briefly described, a calorimetry system embodying the invention has combustion means into which the fuel under test (which may be a solid fuel such as coal) and a gas which will support combustion (oxidizing), such as air are fed for converting the fuel into combustion gas. Means are provided for mixing the combustion gas with another cooling gas, such as air, to provide a combined gas. Means are provided for measuring the temperature of the cooling gas and the combined gas at the inlet and outlet ends, respectively, of the mixing means as well as for measuring the mass feed rate of the fuel into the combustor. Computer means are provided which are responsive to the measurements for computing the heat content of the combustion gas, taking into account the contribution to specific heat of the mass fractions of the components of the combustion gas, data with respect to which may be stored in the memory of the computer. Therefore, accurate data respecting the heating value of the fuel can be determined on the basis of the continuous absolute measurements of the temperatures and mass flow rates of the materials used in the measurement.

Heat loss in the combustor and in the mixing apparatus is avoided by convecting the radiant heat from the combustor and from the mixing process into air flow which is returned to the combustor and to the mixing process. Such return may be accomplished by a cell of porous insulating material surrounding the combustion chamber through which the oxidizing gas (secondary air) is convected into the combustion chamber. A labyrinth passage around the mixing apparatus for the cooling air returns the radiant heat by convecting the cooling air back into the mixing chamber.

Solid fuel such as coal is pulverized and fed at controlled rates to a gravimetric feeder and to an eductor, which is driven by primary air, into the combustor. The mass of the pulverized fuel is measured at the gravimetric feeder together with the feed rate for use in the heating value computation in the computer. During initialization, the feed rate of the coal is gradually increased while the rate of a fuel gas which preheats and initiates combustion of the coal is decreased until self-sustained combustion takes place in the combustor.

The foregoing and other objects, features, and advantages of the invention, as well as a presently preferred embodiment thereof will become more apparent from a reading of the following description in connection with the accompanying drawings in which:

In general the on-line, continuous calorimeter system shown in the drawings has three major components: (a) a materials infeed system which is primarily mechanical, shown principally in FIG. 1; (b) a data acquisition and computer control system, shown principally in FIG. 3 which is primarily electronic; and (c) a thermodynamic calorimetry unit, shown principally in FIG. 2, which is primarily for the flow of mass and energy and their relative balance during measurement.

Figure 1:
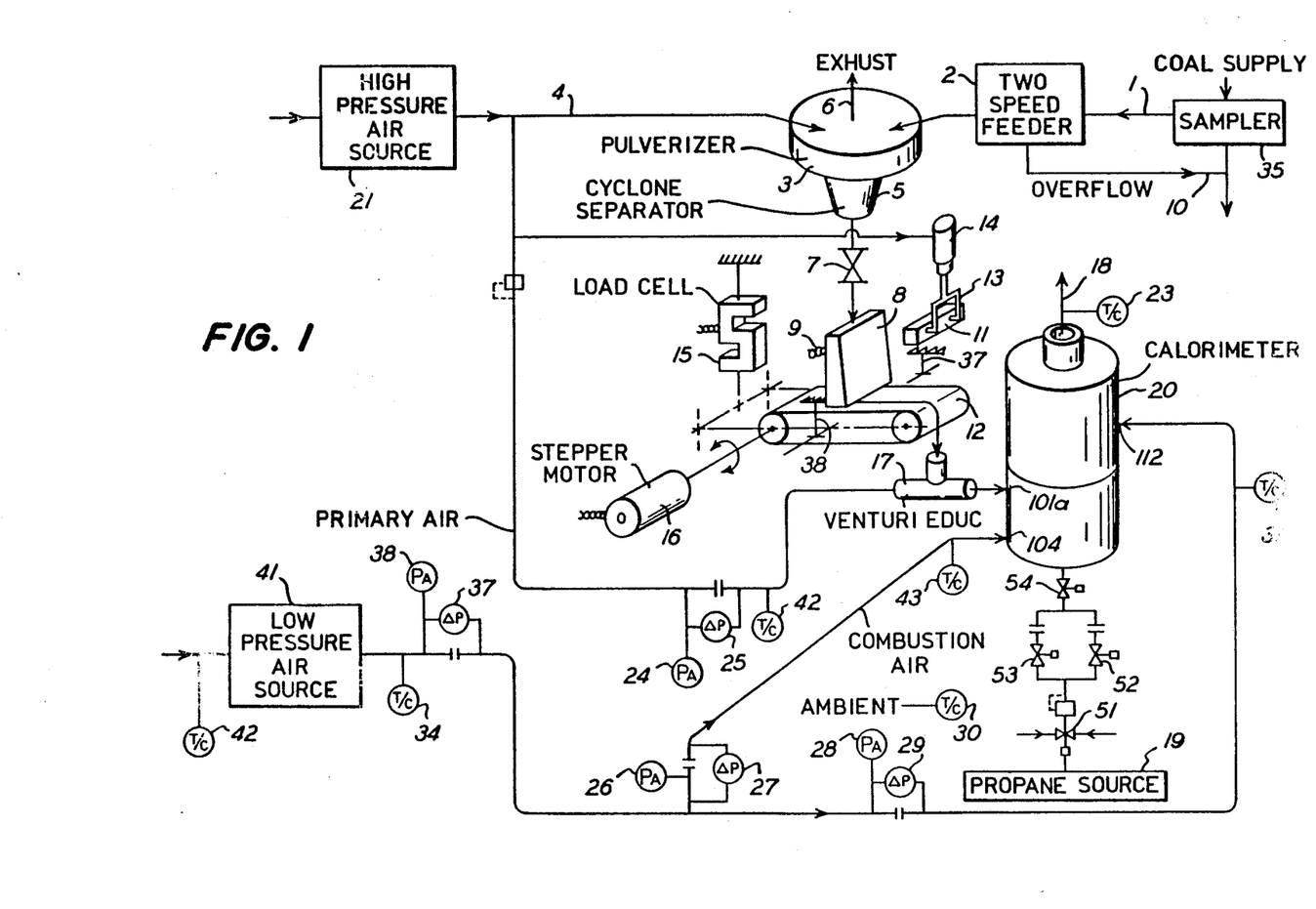
FIG. 1 is a schematic diagram of a calorimetry system embodying the invention.

Referring to FIG. 1, coal is received from the main coal supply 1, for example at sixteen mesh or smaller and its rate of entry into the pulverizer is controlled by a two speed feeder 2. This feeder has three modes of operation: off; feeding at 75% of the nominal capacity of the system (0.75 gram per second); or feeding at 125% of the nominal capacity of the system. Initially, the feeder operates at the higher rate.

Figure 3A:
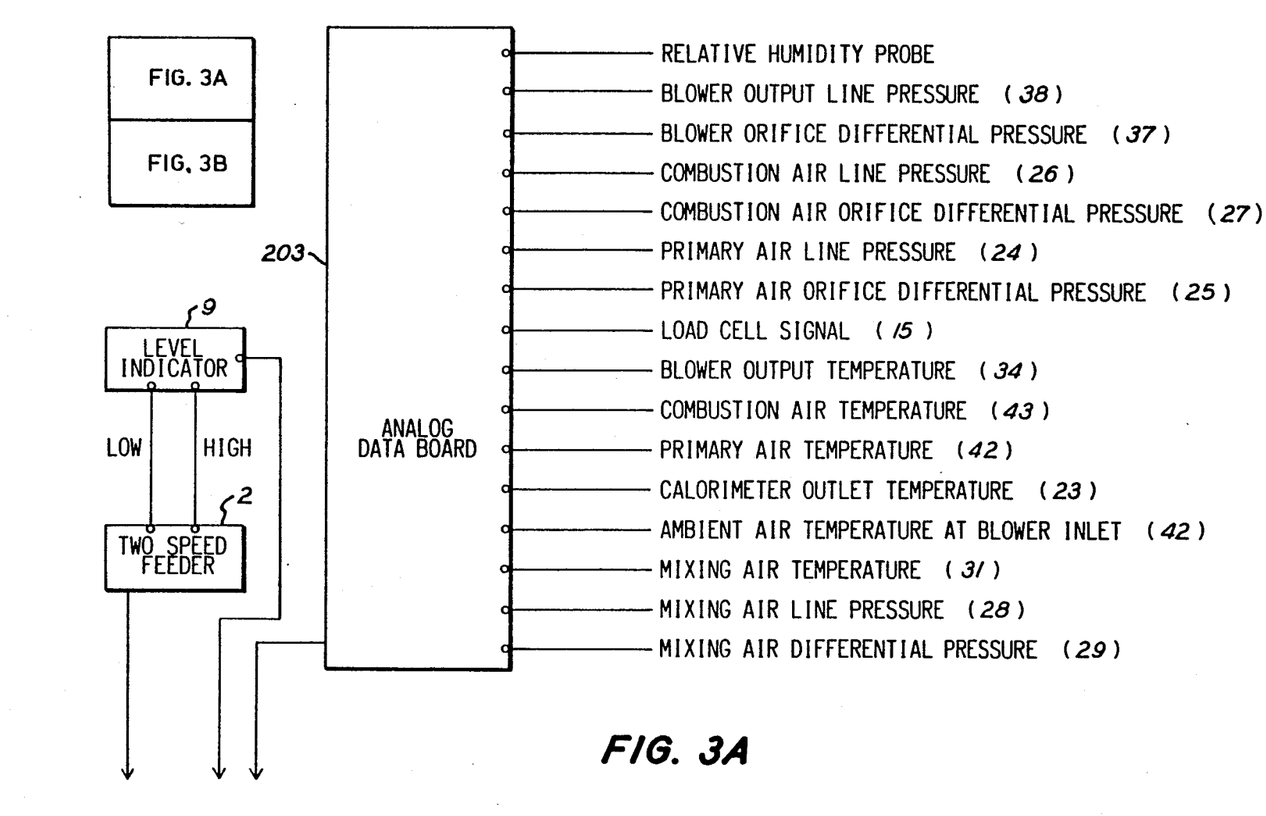
FIG. 3A-3B are block diagram of the electronic computer control and measurement system which are used in the calorimetry system shown in FIG. 1.
Figure 3B:
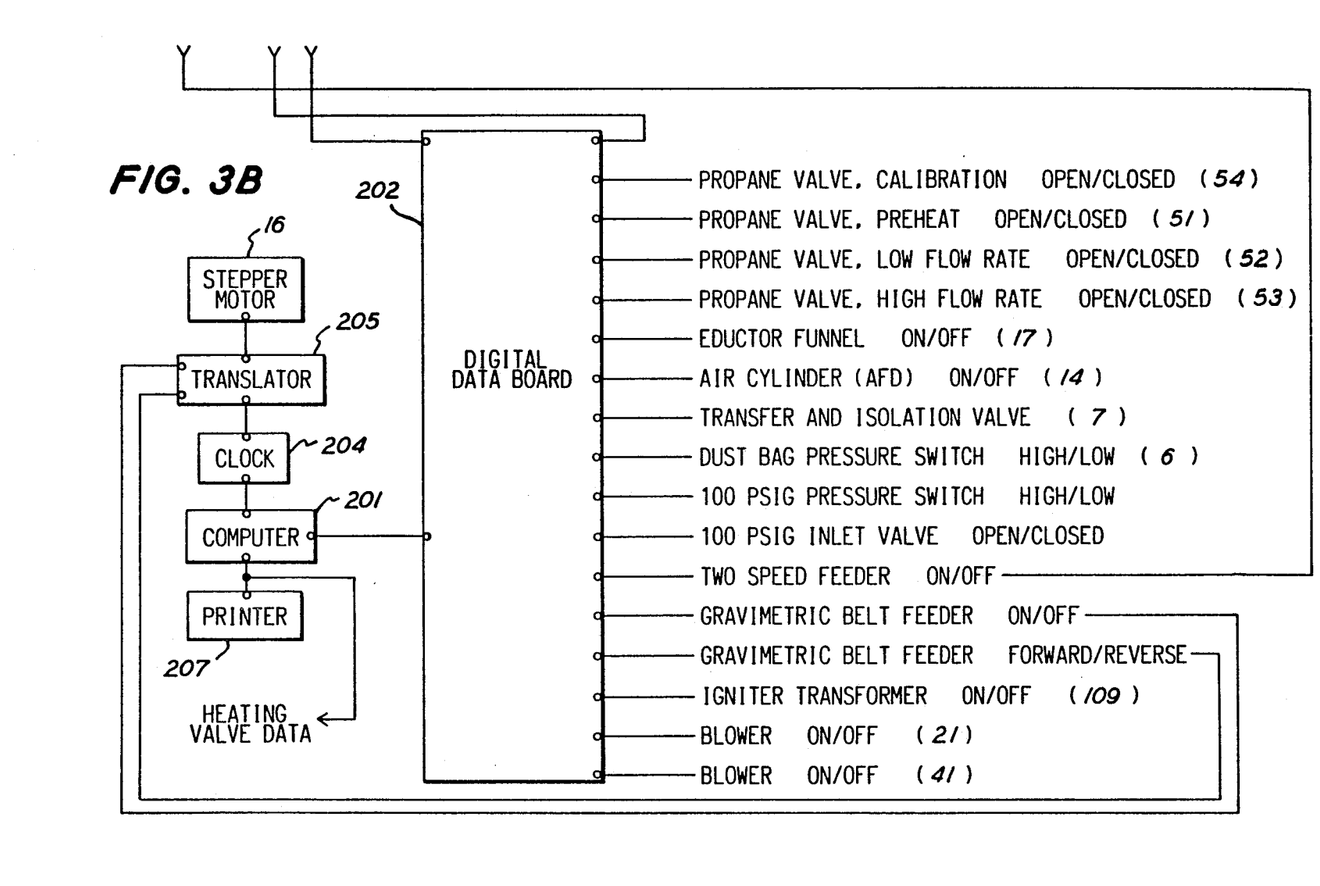

Coal enters a pulverizer 3, from the coal supply continuously via a sampler 35, and is ground by attrition to a dust-like particle size, e.g., of 325 mesh or smaller. The pulverizer 3 is driven by high pressure air 4 from a source (compressor) 21 and, e.g., consumes 20 scfm at 100 psig. There are pressure switches and valves (not shown) connected to the computer system for monitoring this compressor 21 and turning it on and off (FIG. 3). The ground coal is separated from the process air by a cyclone 5 which is an integral part of the pulverizer. The spent process air leaves the system at an exhaust 6, as through a dust collector bag (not shown) which traps any small particles that are entrained in the air stream. Coal leaves the pulverizer by falling out of the bottom of the cyclone 5 and entering the cavities of an isolation and transfer valve 7. This valve prevents the high pressure exhaust air at the pulverizer solids exit from over pressurizing a gravimetric feeder hopper 8.

As the micropulverized coal fills the feeder hopper 8 on the gravimetric feeder 12, its level is sensed by a level detector 9. See also FIG. 3. When the sensor indicates that the coal has filled the hopper to a predetermined level, a signal is sent to the computer 201 (FIG. 3) via a digital data input/output board 202 which causes the two speed feeder to shift to the lower feed rate. Rejects 10 from the two speed feeder are returned to the main coal stream. When enough coal has left the hopper, the level detector 9 deactivates and the two speed feeder returns to the higher feed rate. The hopper on the gravimetric feeder is built with a negative draft (e.g., 2 degrees) to promote solids flow. The lower opening of the hopper is closed by an antiflushing dam 11 to prevent loss of coal when it is first introduced into the hopper. The dam is removed by driving the belt 12 forward until the dam engages a pair of lifting hooks 13 and then is lifted from the feeder belt by the positive action of an air cylinder 14. The dam is held in this position until the hopper is run empty and is put back in place by deactivating the air cylinder and running the belt in the reverse direction until the dam again blocks the lower opening of the hopper.

The feeder belt mounting frame is suspended from two flexures (diagrammatically shown at 25 and 27) which permit a leverage action of the frame. The mass of the coal on the belt provides a downward force on one side of the flexure pivot which is translated to an upward force on the opposite side of the flexure. This upward force is applied directly to a load cell 15 (e.g., 50 gram capacity). In load cell terminology the capacity of the load cell is presented as the mass which represents the upper end of the dynamic range. Because the load cell actually measures force, this mass should be multiplied by the acceleration due to gravity. For example, if the force limit is 4900 dynes, and if the ratio of the two moment arms of the feeder frame is approximately three, when there is seven grams of coal on the belt, a force of about 1960 dynes is applied to the load cell. The output of the load cell is converted by its in line amplifier to a 4–20 ma output which is transmitted to the data acquisition system (analog data board 203 in FIG. 3).

The feeder belt is driven by a stepper motor 16 whose controlling frequency is generated by the computer (FIG. 3). If the mass feed rate indicated by the load cell does not match with the desired feed rate, a compensating change in frequency is calculated by the computer and transmitted to the frequency source (CLOCK 204—FIG. 3) which in turn sends an altered signal to the translator 205 (FIG. 3) and the stepping rate of the motor 16 is increased or decreased as needed. The mass feed rate is therefore kept constant. The stepper motor is attached to the feeder belt mounting frame and its mass is compensated by a counterweight at the forward end of the feeder (not shown).

Micropulverized coal drops off the end of the belt and is suspended in the primary air supply coming from the high pressure air source 21 by entering a venturi eductor 17. A vibrating funnel (not shown), promotes coal flow. The amount of air driving the venturi is equal in flow to the total required for primary air.

The coal and air mixture enters the calorimeter 20 by being distributed, via an inlet pipe 101a, through an annular manifold 101 with three equally spaced slot openings 103 at the top of a combustion chamber 102. See FIG. 2. The calorimeter 20 has the combustion chamber at its lower end 130 and an air mixer unit 132 at its upper end. The flow path of the coal from the manifold 101 is folded back on itself and the burning of the coal takes place in the centroid of the chamber 102. Secondary air to an inlet pipe 104 is provided by a high volume, low pressure air supply source (blower) 41 (FIG. 1), operating e.g., at 30 to 40 inches of water column. There are switches and gauges for monitoring this blower and turning it on and off, connected to the computer system (FIG. 3).

This secondary air gains access to the combustion chamber 102 by passing through a porous insulator cell 105 of fire brick ceramic material, surrounding the chamber 102. The insulator 105 is heated by radiative and convective loss from the combustion chamber 102 and is cooled by the secondary air passing through it. During this passage, the secondary air is heated, picking up the radiant and convective heat loss from the chamber 102, before entering the combustion chamber through a set of circumferential holes 108 plus three holes (not shown) equally spaced and located at the bottom of the inverted cone of the chamber 102. See also FIGS. 5, 5A and 5B.

Prior to introducing the coal and air mixture into the combustion chamber, a period of preheating is accomplished by burning propane which enters via a pipe 123 at the apex of the cone. The gas is injected from a source indicated at 19 (FIG. 1), via a flow control system of four valves 51-54, into the combustion chamber. Alternatively, the same manifold 101 used for the coal and primary air mixture may be used. The propane is ignited by a spark igniter 109, also located near the centroid. Once ignition of the propane has been ascertained by a rapid increase in the temperature of the exhaust gases (as measured by a thermocouple (T/C) 23 at the outlet 18 of the flue of the calorimeter 20 (FIG. 1), the igniter is deactivated.

The computer 201 receives this thermocouple 23 signal via an analog data board 203 (FIG. 3), which contains analog to digital converters. This board also receives signals from pressure gauges 24-29, and 37, 38 which measure absolute and differential pressures ($P_A$) and ($\Delta P$) and other thermocouples. The digitized signals from the board 203 are multiplexed with other digital inputs to the digital board 202 and supplied to memory in the computer 201. The entire apparatus, combustion chamber end 130 plus air mixer end 132, is heated by the burning propane. This preheat cycle is complete when the rate of increase in the exhaust gas temperature is near zero.

The flow of coal is initiated at 100 percent of the nominal value and, when a new thermal equilibrium position is reached, the flow of propane is gradually reduced. When the flow of propane is completely stopped, the calorimeter establishes a new equilibrium position for the unsupported, self-sustaining combustion of coal. During this mode of operation, ignition of the coal occurs by preheating of the coal and primary air mixture due to radiative heating from the fireball in the centroid of the combustion chamber.

Combustion of the coal is completed within the combustion chamber except during the period when both coal and propane are flowing. Under that condition, some combustion appears to be completed in the air mixer. This is the reason for the gradual reduction in propane flow rather than total, immediate cessation. The fireball must be retracted slowly into the combustion chamber. With it partially in the combustion chamber and partially in the air mixer, there is insufficient radiative heat flow to preheat the incoming coal and the mass of the combustion chamber is not up to operating temperature. Too rapid a retraction of the fireball under these conditions results in quenching of the flame due to inadequate preheating.

Once a new equilibrium condition is achieved with an unsupported coal flame, the calorimeter can be used to determine the heating value of the coal. The coal is delivered to the calorimeter through the openings 103.

Figure 2:
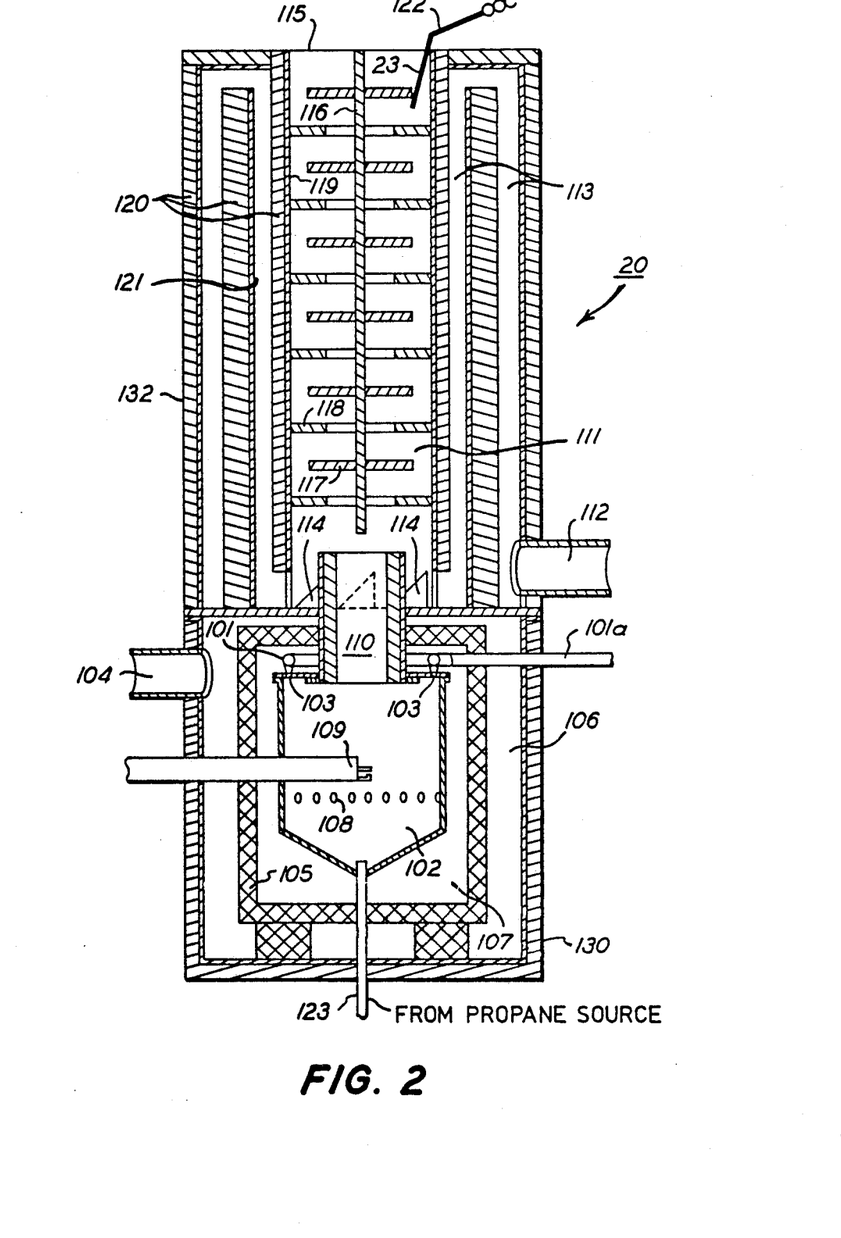
FIG. 2 is a schematic transverse sectional view of the calorimeter used in the system shown in FIG. 1.

The air to support combustion enters the calorimeter through the pipe 104 and passes through the porous thermal insulator 105. The porous insulator serves a twofold purpose; it prevents heat loss from the combustor and, because the air passes from the outside plenum 106 to the inside plenum 107, it absorbs heat prior to entering the combustion chamber 102. The increase in the air temperature facilitates the maintenance of the combustion reaction.

The pathway 140 followed by the coal in the combustor 102 is downward near the outside wall of the combustor and upward near the center. See FIGS. 5, 5A and 5B. Secondary combustion air enters the combustor through the ring of openings 108 below the midline of the combustor body. The combustion reaction is initiated by activating the igniter 109, such as a spark plug or a glow bar electrically heated via a transformer (not shown) to turn it on (see control output from digital data board 202—FIG. 3) or a flame, which can enter radially or vertically as long as the spark or flame is in the centroid of the combustion chamber. After combustion has become self-sustaining the igniter is deactivated. At that point the incoming coal and air are heated by radiation from the fireball in the chamber 102.

Figure 5:
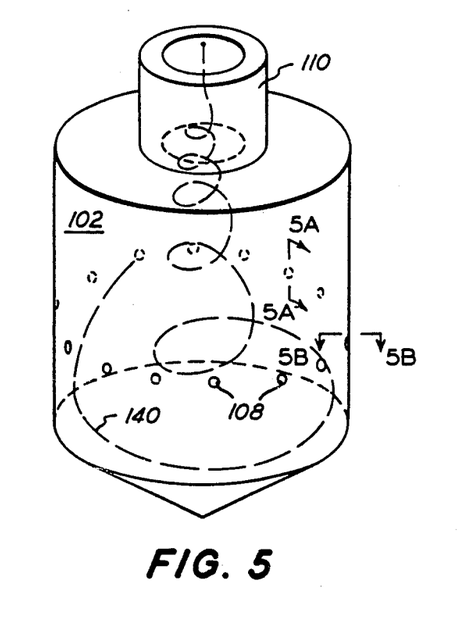
FIG. 5 is a diagrammatic and perspective view of the combustor of FIG. 2, showing the pattern of flow of the material therein caused by the tangential air entry therein.
Figure 5A:
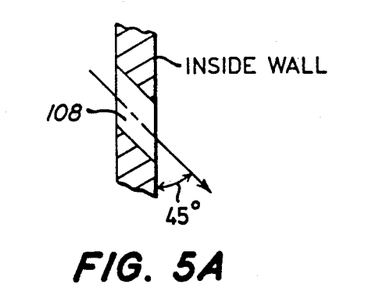
FIGS. 5A and 5B are fragmentary sectional views taken along lines 5A—5A and 5B—5B in FIG. 5.
Figure 5B:
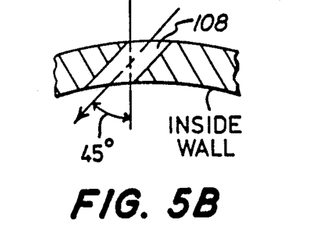

The holes 108 provide tangential air entry to the combustor 102. As shown in FIGS. 5, 5A and 5B the penetration through the side wall of the combustor is downward and rotated away from a radial line by 45 degrees. This achieves several things: first, the air flow hence fuel flow path is lengthened thereby increasing residence time of coal particles. As air moves inward and upward coal particles are thrown back toward the wall until only ash remains. The ash is now a very fine particle that is carried by the exhaust gas out of the combustor. Second, the downward flow also helps to sweep away ash from the bottom cone and entrain it in the upward moving flue gas. This keeps the combustor clean and provides a means for later capturing the flue ash for ash determination in the coal.

Figure 6A:
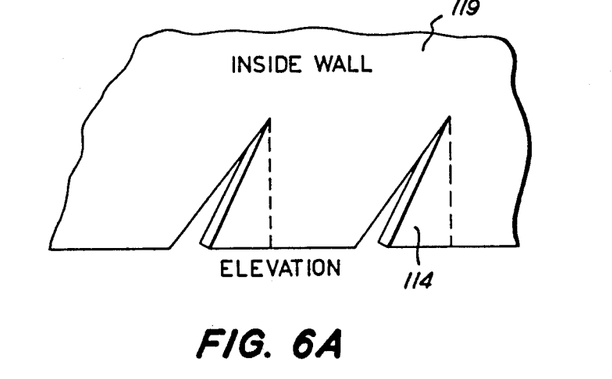
FIGS. 6A and 6B are a fragmentary elevational and a fragmentary plan view from the bottom respectively of the lower end of the mixing chamber shown in FIG. 2.
Figure 6B:
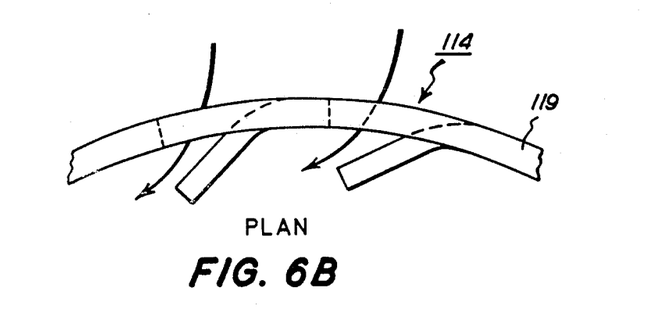

The hot products of combustion (combustion gas) exit the combustion chamber through opening 110 and enter the mixing chamber 111. The cooling or mixing air enters the calorimeter through pipe 112 and travels through a labyrinthine plenum 113, and enters the mixing chamber 111 through a number of entry baffles and openings 114 at the base of the wall of a tube 119 defining the mixing chamber 111. See FIGS. 6A and B. These openings 114 are generally triangular and are disposed around the neck of the pipe which extends between the combustion unit 130 and mixing unit 132. This provides a cycloidal flow which aids mixing. The cooling air in the plenum picks up the radiative heat losses from the mixing chamber and returns that heat to the mixing chamber, thereby increasing the accuracy of measurement. Specifically the openings 114 are formed by cutting along the hypotenuse of the triangle and bending inward along the vertical side of the triangle. This provides an entry and baffle that guides the mixing air along an upward helical path which aids mixing with flue gas and reduces the pressure drop across the labyrinth and the mixing chimney 111.

The hot combustion products and the cooling air mix by turbulent flow while traveling the length of the mixing chamber and exit the calorimeter at exhaust vent 115. Mixing of the combustion products and the cooling air is further enhanced by the presence of baffles 116. In this embodiment, the baffles are comprised of an alternating series of discs 117 and rings 118 which increase the turbulence of the flow. The thermocouple probe 122, having the thermocouple 23 at the top of the calorimeter, enters the vent and is located between the last (uppermost) baffles. This disposition of the thermocouple isolates the thermocouple 23 at the exhaust outlet from the combustion chamber and its flame to prevent temperature measurement errors due to radiant heating of the thermocouple. The mixing apparatus can be either static or dynamic, i.e., the discs 117 can be moved with respect to the rings by a suitable actuator such as a vibrator.

The calorimeter operates in accordance with the First Law of Thermodynamics. In this embodiment of the invention, the rate of fuel delivery and the rate of energy release are both measured continuously and the heating value is from the equation:

$$\text{heating value} = Q/M_f \qquad (1)$$

If Q, the rate of energy release, is given in BTU/hr and $M_f$, the rate of fuel flow, is given in LB/hr, then their quotient is the heating value of the fuel in BTU/LB. Other suitable units are applicable, such as kJ/kg.

The value of Q, the energy release rate, is determined by applying the method of mixtures in accordance with which the heat lost by the combustion products (material under test or fuel) is gained by the cooling air. For accurate measurement, it is necessary that the heat losses from the calorimeter be minimized to the greatest possible extent. This is achieved first, by the porous insulator cell 105 which blocks the loss of heat from the combustion chamber. By absorbing this heat, the insulator itself becomes hot. This heat is recovered by passing the secondary combustion air through the insulator which causes the combustion air to absorb the heat of the insulator and transfer it back to the combustion chamber.

Second, heat losses from the mixing chamber are minimized by the labyrinthine pathway of the cooling air. Heat passes from the mixture of combustion products and cooling air to the metal tubular wall 119 of the mixing chamber 111 by convection and, similarly, to the layer of insulation 120 surrounding the mixing chamber. The cooling air flows along the surface of this insulation starting at the low temperature end and gains heat as it travels downward to the entrance 114 of the mixing chamber. Because there is also a heat loss from this surface by radiation, a second insulation surrounded metal cylinder 121 is provided. By a similar action, air travels upward from the entrance to the pathway 112, past the surface and recovers any heat absorbed by the cylinder 121. The entire exterior surface of the calorimeter is covered with insulation of a suitable type.

The heat absorbed by the cooling air is equal to the heat lost by the combustion products. The amount of this heat can be calculated by:

$$Q_a = M_a \times C_p \times (T2 - T1) \qquad (2)$$

where
  $Q_a$ = heat flow in BTU/hr;
  $M_a$ = Mass flow of the cooling air in LB/hr;
  $C_p$ = Specific heat of air in BTU/(LB×deg-F);
  $T2$ = Temperature of the mixture at the exhaust vent 115 in deg-F
  $T1$ = Temperature of the cooling air at the entrance to the pathway 112 in deg-F.

Because the mixture of combustion products and cooling air leaves the calorimeter at an elevated temperature, a similar calculation is performed to determine the heat content of the mixture compared to the heat content of ambient air. This calculation is performed by making the assumption that the thermodynamics of the exhaust combustion gases are the same as those for air. This assumption is reasonable because of the approximately 50-fold excess of air over the combustion gases. The sum of these two computations is equal to the total heat flow from the combustion reaction to the cooling air. The heating value of the coal is calculated by the use of equation (1) as described above.

Because combustion is completed within the combustion chamber, all of the energy available by burning the coal is released there and absorbed by the products of combustion, excess air, and inert gases passing through the system. Absorbing this heat, it is estimated, raises the temperature of these gases to the range of 1800–2000 degrees F. The hot gases leave the combustion chamber and enter the air mixer where they are mixed with a large excess of cooler air (e.g., 185 deg F. at 165 scfm). This entire mixture of hot combustion products and cool mixing air then leaves the calorimeter at a temperature in the range of 380–460 deg F. Since the mass flow rate of the mixing air is computed from its pressure measurement and inlet temperature, and the rate of coal feed is computed from load cell signal at the constant belt speed, the heating value data is computed by the computer 201 in accordance with equation (2) and (1).

The instrumentation allows for the measurement of the heating value without relying on the assumption that the thermodynamics of the mixing air and exhaust combustion gases are the same. This is because the pressure gauges and thermocouples provide for accurate computation of the mass flow of the primary air and the combustion air as well as the feed rate of the coal. The nonlinear effect of the specific heat or heat capacity ($C_p$) of the constituents of the combustion products can then be taken into account. Consider that the heat flow Q can be computed more accurately from the following equation:

$$Q_c = (m_{coal} + m_{air}) \int_{T_1}^{T_2} C_{pf} dT \qquad (3)$$

$C_{pf}$ is a composite function taking into account the average mass fraction of each flue gas (combustion product) component for a given rank. For coal and air these are $CO_2$, $H_2O$, $SO_2$, $N_2$, $O_2$ and ash. It has been discovered that within a given rank of coal, bituminous, subbituminous, lignite, etc., the heat capacity of the combustion products is nearly the same. Therefore, since the type of coal is known, data on the heat capacity of the rank to which the coal is associated is stored in the memory of the control computer 201 and used to improve the heat calculation. The following provides a more detailed explanation of the proceeding: From equation 3, coal heating value in BTU/lb. is derived from the first law of thermodynamics where both m coal and m air (mass flow rates), are measured accurately (mass/unit time) as are $T_1$ and $T_2$ from thermocouples 31($T_1$) and 23($T_2$). Heat capacity (specific heat) of flue gas $C_f$ is a complex function of temperature and varies with the gas make up.

Figure 4:
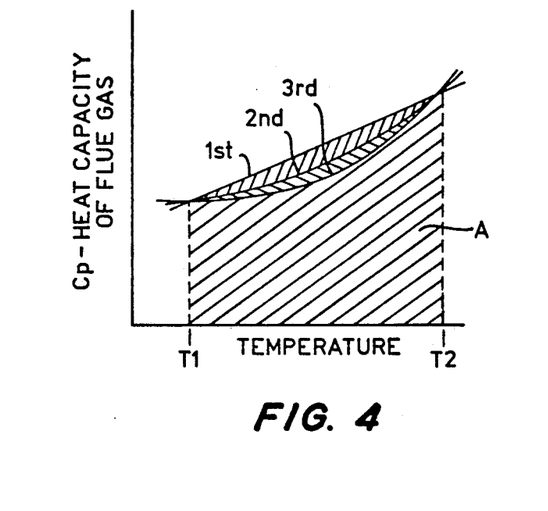
FIG. 4 is a curve illustrating how the system accurately takes into account the specific heats (heat capacity) of the constituents of the combustion or flue gas which is used in the measurement process.

A first approximation assumes a straight line relation between $C_p$ and T (see FIG. 4). Error includes the area between line 1st and curve 3rd.

A second approximation assumes heat capacity of air only and results in the error between curves 2nd and 3rd.

A third approximation accounts for the gas make up where the average mass fraction within a given rank of each gas component is considered. Within a given coal rank i.e. bituminous coal, the flue gas specific heat has been found to be the same. Therefore taking into account the nonlinearities in Cp for each component the product $Cp(T_2-T_1)$, which is the area under the curve, can accurately be determined, as can the heat flow $Q_c$. See the following table.

| Component | Heat Capacity | Mass Fraction |
|---|---|---|
| $CO_2$ | $Cp_{CO2} = a_1 + b_1T + c_1T^2 + d_1T^3$ | $x_1$ |
| $H_2O$ | $Cp_{H2O} = a_2 + b_2T + c_2T^2 + d_2T^3$ | $x_2$ |
| $SO_2$ | $Cp_{SO} = a_3 + b_3T + c_3T^2 + d_3T^3$ | $x_3$ |
| $N_2$ | $Cp_N = a_4 + b_4T + c_4T^2 + d_4T^3$ | $x_4$ |
| $O_2$ | $Cp_{O2} = a_5 + b_5T + c_5T^2 + d_5T^3$ | $x_5$ |
| Air | $Cp_{air} = a_6 + b_6T + c_6T^2 + d_6T^3$ | $x_6$ |
| Ash | $Cp_{ash} = a_7 + b_7T + C_7T^2 + d_7T^3$ | $x_7$ |

Therefore, the heat capacity of the total flue gas is given by:

$C_{pf} = W + XT + YT^2 + ZT^3$ and $W = a_1X_1 + a_2X_2 \cdots a_7x_7$ $X = b_1X_1 + b_2X_2 \cdots b_7x_7$ etc. Finally, $$\int_{T_1}^{T_2} C_{pf} dT = \int_{T_1}^{T_2} (W + XT + YT^2 + ZT^3) dT \qquad (4)$$

It will be observed that the composite $C_{pf}$ is the area, A, under the curve, 3rd, in FIG. 4.

The number of ranks of coal are limited to 5 or 6, therefore, the coefficients a,b,c, etc. can be stored conveniently. Calculations are carried out, on line, at intervals of about five seconds by the control computer. Results can be averaged over any interval greater than five seconds as desired.

The data acquisition and computer control system (FIG. 3) has the function of collecting and processing all of the input and output signals, performing all of the calculations, and controlling the operation of the various motors, accuators, and solenoid valves, as discussed above. It has five basic modes of operation: (1) automatic startup and calibrate, (2) calibrate on demand, (3) standby, (4) analyze, and (5) automatic shutdown. There is also a safe shutdown on failure mode which is invoked whenever an equipment failure occurs.

The automatic startup and calibrate mode is initiated by turning on the power to the unit. This activates the computer and applies power to all of the electronic components. When fully functional, all of the data collecting transducers (T/C and pressure gauges) are operational and report the status of their test points to either the analog 203 or the digital 202 data board. (FIG. 3). The first test made by the computer is whether the high pressure air supply is at the minimum pressure of 100 psig. If true, then the high pressure air supply shutoff valve is opened. If not true, then an error message is sent to a printer 207. After the high pressure air is admitted to the unit, the low pressure blower 41 is activated and, after a delay of a few seconds, the computer tests whether the blower output line pressure is satisfactory. If not true, then an error message is sent to the printer. If true, then the spark igniter is activated.

Operation of the calorimeter requires two independent gas supplies: a thermodynamically analyzed gas to be used for calibrating the unit and any combustible gas (e.g. propane) available in large quantities for preheating the system. Then, after the igniter is activated, the preheat gas shutoff valve is opened and the preheat gas enters the combustion chamber and is ignited. Ignition is tested by an increase in the temperature of the exhaust gas. If ignition is not confirmed, an error message is sent to the printer. If ignition is confirmed, the spark igniter is deactivated. The computer tests the temperature of the exhaust gas to determine whether the unit is up to the operating condition. When the unit has achieved the appropriate operating temperature, the preheat gas shut off valve is closed and the calibrate gas shut off valve is opened. By measuring the mass flow rate of the calibration gas and the heat flow rate due to its combustion (described above), the heating value of the calibration gas is determined and sent to the printer. The results of the calibration are compared to the known heating value of the calibration gas and the decision is made to either continue the run or to shut down and make corrections. After the calculated heating value of the calibration gas has been sent to the printer, the calibration gas shut off valve is closed and the preheat gas shut off valve is opened. The unit is now in the standby mode and ready to start analyzing fuel on operator demand.

The analyze mode is entered by depressing the appropriate push button on the unit (on a panel or computer keyboard—not shown) and can only be accessed from the standby mode. After the initiating conditionals are ascertained to be satisfied, the eductor funnel solenoid at 17 is energized and the transfer and pressure isolation valve 7 is activated. The two speed feeder 2 which feeds the pulverizer 3 is started at the higher feed rate. With these pieces of equipment in operation, the solid fuel enters the pulverizer and is ground to a desired particle size (e.g., 325 mesh or smaller). The micropulverized coal is received by the transfer and pressure isolation valve 7 and delivered to the hopper 8 on the gravimetric belt feeder 12. This hopper 8 has a negative draft (e.g., of two degrees) to promote the flow of micropulverized solid fuel out of the hopper. When the level of solid fuel in the hopper rises high enough to cause the level sensor 9 to change its state, a signal is sent to the two speed feeder 2 to shift to its lower feed rate. At the lower feed rate, the solid fuel level in the hopper decreases until the level sensor 9 is deactivated and changes back to its former state and the two speed feeder is shifted again to the higher feed rate. The rate at which the belt feeder removes solid fuel from the hopper is intermediate between the higher and the lower feed rates of the two speed feeder. Thus, the rate of solid fuel delivery by the belt feeder indirectly controls the rate of solid fuel introduction into the unit.

The first time the level indicator causes a shift in the two speed feeder feed rate, a signal goes to the computer to begin operation of the gravimetric belt feeder. The first operation which must be done is the removal of the antiflushing dam 11. The purpose of the dam is to prevent the free flow of micropulverized solid fuel from the outlet of the belt feeder hopper. The dam is removed by advancing the feeder belt until the dam engages the tines of the lifting mechanism which are attached to an air cylinder. The air cylinder is activated on command from the computer and the antiflushing dam is raised from the feeder belt a distance sufficient to give the bed of solid fuel on the belt an unhindered clearance. The feeder belt drive is restarted and the flow of micropulverized to the calorimeter begins.

The purpose of the gravimetric belt feeder is to measure the mass flow rate of the solid fuel into the calorimeter. This is achieved by flexure-mounting the main belt frame, making it a lever of the first class, and contacting a load cell with the short moment arm of the lever.

The bed of solid fuel lying on the belt causes a downward force on the long moment arm of the lever which causes an upward force on the load cell. The difference in the length of the two moment arms results in a multiplication of the force exerted by the solid fuel on the belt. The load cell sends a signal proportional the force exerted on it to an in line amplifier. The in line amplifier (not shown) converts the load cell signal proportionately to a 4–20 ma signal and transmits it to the analog data board 203.

The signal is encoded by the A/D converter on the board 203 and sent to the computer via the digital board 202 (multiplexed with other inputs), where it is compared to an established value equivalent to a certain solid fuel flow rate (e.g., of 0.75 gram per second). If the signal sent by the load cell indicates that the solid fuel flow rate is less than 0.75 grams per second, then the belt speed is increased and, conversely, if the indication is that the feed rate is too high, then the belt speed is reduced.

The feeder 12 belt is driven by the stepper motor 16 whose stepping rate is controlled by the frequency dependent translator 205. The translator converts the frequency into a series of switching operations which energizes various stator fields in the stepper motor causing it to turn at a rate which is proportional to the frequency. The controlling frequency is produced by a programmable signal generator (counter) in the translator 205 driven by the clock 204. The change in the frequency of this signal is determined by the amount of offset between the established load cell value and that actually reported by the load cell 15 on the belt feeder. It is the actual load cell value that is used by the computer to calculate the mass flow rate of the solid fuel.

When the solid fuel reaches the end of the belt feeder, it falls off the end of the belt and into the vibrating eductor funnel 17. The eductor funnel can vibrate to promote the flow of solids into the eductor. The venturi nature of the eductor serves also to induce solids flow. Once the micropulverized fuel enters the eductor, it is suspended in the primary air supply of the calorimeter and combustion proceeds as described above.

When the solid fuel begins to burn in the combustor, a new thermal equilibrium point is attained as indicated by the temperature of the exhaust gases. After this point is reached, a phased shut off of the preheat gas is begun. This is to allow a timely shift to a new thermal equilibrium that is unique to the combustion of the solid fuel unsupported by the preheat gas. Initially, both of the preheat gas flow rate control valves are open, giving full flow. The phased shut off begins by closing the low flow rate valve reducing the preheat gas flow rate to about two-thirds of its full flow rate value. As a new thermal equilibrium is identified, the high flow rate valve is closed and the low flow rate valve is opened, giving a flow rate of about one-third the full flow rate value. Establishing a new thermal equilibrium results in the closure of the low flow rate valve and, after establishing the final equilibrium, the solid fuel burns unsupported by the preheat gas. At this point, by measuring the total mass flow rate of air, the mass flow rate of the solid fuel, and inlet and exit temperatures, the heating value of the fuel is calculated as outlined above. This set of calculations is repeated on a periodic basis until the standby mode or the automatic shut down mode is invoked. In the event that the fuel supply is exhausted, the standby mode is entered.

The calibrate on demand mode of operation is accessed by depressing the appropriate panel or keyboard push button. This sends a signal to the computer to suspend operation and initiate the calibration sequence. If the unit is currently analyzing fuel, the analysis is stopped. If the unit is in the standby mode, the support gas source is switched from preheat gas to calibrate gas. The calibrate on demand mode cannot be entered from the automatic startup or the automatic shutdown modes. When the calibrate on demand mode is entered from the analyze mode, the first step is to shut off the two speed feeder which is delivering fuel to the pulverizer. Then the transfer and pressure isolation valve is stopped. The gravimetric belt feeder is stopped but the eductor funnel solenoid is left activated. When the exhaust temperature indicates the combustion of coal has ceased (presumably by exhausting the combustor inventory), the eductor funnel solenoid is deactivated and the calibrate gas shut off valve is opened. This would be the point at which the calibrate on demand mode would be entered from the standby mode. After the calibrate gas shut off valve has been opened, the exhaust temperature is tested to determine whether ignition has occurred. If ignition is not indicated, then an error message is sent to the printer. If ignition has taken place, then a period of time is allowed to establish equilibrium and the heating value of the calibration gas is determined and reported as described above. Once the measurement of the calibration gas is complete, the calibrate gas shut off valve is closed and the preheat shut off valve is opened and the units remains in the standby mode after sending a message to the printer. This state is maintained pending further instructions from the operator.

The automatic shut down mode is invoked by depressing the appropriate push button on the unit control panel or keyboard. When the automatic shut down mode is entered, the first piece of equipment to go off line is the two speed feeder which feeds the pulverizer. The decrease in the temperature of the exhaust gases indicates when the coal inventory in the unit has been consumed and the remaining components can be deactivated. The gravimetric belt feeder is stopped and the antiflushing dam is replaced. The eductor funnel solenoid is deactivated and the high pressure shut off valve is closed. The low pressure blower continues to operate until the exhaust temperature indicates that the unit has reached its minimum temperature and then is shut off. A shut off message is sent to the printer and the low voltage power supply is turned off. The computer deactivates itself and shut down is complete.

From the foregoing description, it will be apparent that an improved system for accurate, continuous, calorimetry of solid fuel can be accomplished. Because the thermal capacity of the system is low, (heat retentive masses are limited) temperatures can change quickly and the system can respond quickly to changes in the heating value of the solid fuel. The system is especially adapted to the control of furnaces in coal or other solid fuel fired power generating plants, and the output heating value (BTU/LB) can be directed not only to a printer, but also on-line to the control system of the coal feeder for the furnace (e.g. of the steam generator), thereby conserving fuel and reducing the fuel cost of power generation. Variations and modifications in the herein described system as well as other applications therefore, will undoubtedly suggest themselves to those skilled in the art. Accordingly, the foregoing description should be taken as illustrative and not in a limiting sense.

We claim:

1. A calorimetry system for measuring the heating value of a fuel comprising combustion means into which said fuel and oxidizing gas are fed for converting said fuel into combustion gas, means for mixing said combustion gas with a mixing gas to provide a combined gas, means for measuring the temperature of said mixing gas, and said combined gas at the inlet and outlet of said mixing means, respectively, said oxidizing and said mixing gas being parts of a total gas means for measuring the mass feed rate of said fuel fed into combustion means, means for measuring the mass flow rate of said total gas, computer means for computing the heat flow $Q_c$ of said combustion gas in accordance with the equation $$Q_c = (m_1 + m_2) \int_{T_1}^{T_2} C_{pf} dT$$

where $m_1$ is the mass feed rate of the fuel, $m_2$ is the mass feed rate of the total gas, $T_1$ is the temperature of said mixing gas at said inlet, and $T_2$ is the temperature of said combined gas at said outlet, and $C_{pf}$ is the specific heat of said combined gas represented by a polynomial whose coefficients are the weighted sum of coefficients of similar polynomials that represent the specific heat of constituents of the combined gas over the temperature range $T_2-T_1$, and said computer means also having means for computing the heating value of said fuel as the ratio of $Q_c$ to $m_1$.

2. The system according to claim 1 wherein said computer means has means providing storage for the data representing heat capacity of each constituent of said combustion gas over a temperature range including $T_2-T_1$ for a plurality of different types of fuel.

3. The system according to claim 2 wherein said fuel is coal and said other gas and said oxidizing gas is air, and said computer storage means stores the polynomial coefficients for $CO_2$, $H_2O$, $SO_2$, $N_2$, $O_2$ and ash for a plurality of different ranks of coal which constitute said types.

4. A calorimeter system for the direct and continuous measurement of heating value of fuel which comprises combustion means into which said fuel and an oxidizing gas is fed for converting said fuel into a combustion gas, means for mixing said combustion gas with another gas to form a combined gas, said combustion means comprising a combustion chamber having an outlet for said combustion gas, an inlet for said fuel, and an inlet for said oxidizing gas, a cell of porous insulating material disposed around said chamber for absorbing radiant heat loss from said chamber, and means for communication of said oxidizing gas through said cell with said oxidizing gas inlet of said chamber for convecting said radiant heat back to said chamber, said mixing means comprising a channel having an inlet end in communication with said combustion gas outlet, an outlet end for said combined gas and an inlet for said other gas also at said inlet end, means for absorbing heat from said channel disposed around said channel, said channel heat absorbing means defining a passage for said other gas therethrough for converting the heat absorbed by said channel heat absorbing means back to said mixing means, and means responsive at least to the temperature of said other gas supplied to said mixing means inlet, the temperature of said combined gas at said mixing means outlet and the mass feed rate of said fuel into said chamber for computing the heating value of said fuel.

5. The system according to claim 4 wherein said combustion chamber and said cell are disposed in a housing, the inside of which with the outside of said cell defines a space, and a pipe communicating said oxidizing gas under pressure into said space.

6. The system according to claim 5 wherein said combustion chamber has an upper end with a plurality of openings spaced from each other along an annular path, an annular manifold disposed at said upper end and having a plurality of openings in communication with said annular openings to provide said inlet for said fuel, said fuel being solid fossil fuel, and means for feeding said fuel in particulate form into said manifold and said chamber under pressure.

7. The system according to claim 6 wherein said outlet from said chamber is a pipe defining a chimney extending from said upper end of said chamber, said manifold being disposed around said chimney pipe.

8. The system according to claim 6 wherein said chamber is a cylinder with a conical bottom, a plurality of holes below the midplane of said cylinder for said entry of pressurized oxidizing gas.

9. The system according to claim 8 further comprising an inlet for a gas for preheating said chamber and initiating combustion of said solid fuel therein, and an igniter for said preheating and combustion initiating gas disposed in said chamber.

10. The system according to claim 4 wherein said mixing means comprises a second housing disposed upon a first housing containing said combustion chamber, a pipe in said housing, said pipe defining a chimney providing said channel and extending upwardly, the lower end of said pipe defining said inlet end and having an opening at the bottom of said lower end for said combustion gas and an opening about the side thereof at said lower end for said other gas, an annular member spaced between the inside of said housing and the outside of said pipe defining a labyrinth path around said pipe, said path defining said passage and having said opening about said side of said pipe at said lower end as the outlet thereof and an opening through said housing at the opposite end of said path as the inlet for said other gas.

11. The system according to claim 10 further comprising baffle means in said channel pipe including a plurality of members spaced between the opposite ends thereof.

12. The system according to claim 11 wherein said baffle means members comprise a series of rings having openings therein spaced from each other axially along said channel pipe, and a series of discs spaced from each other axially along said pipe, the diameter of said discs being greater than the openings in said rings and less than the diameter of said channel pipe, and said rings and discs being disposed alternately axially along said pipe.

13. The system according to claim 12 further comprising a thermocouple for measuring the temperature of the combined gas exiting said channel pipe, said thermocouple being disposed between the ring and disc closest to the outlet end of said pipe.

14. The system according to claim 10 wherein a pipe defining a chimney extends from said combustion chamber into the lower end of said channel pipe, and a plurality of openings along the side of said channel pipe at the lower end thereof and provided, baffles extending inwardly of said openings into said pipe, each of said openings being disposed along the lower end of said pipe, a first side extending upwardly from said base to a height not exceeding the extension of said chimney pipe into said channel pipe, and another side extending between the end of said first side and the end of said base.

15. A calorimeter system for the direct and continuous measurement of the heating value of coal which comprises means for converting said coal into a combustion gas, means for mixing said gas with air to provide a combined gas, means to measure mass rate of total air flow, means for measuring at least the increase in temperature between the temperature of said mixing air and the temperature of said combined gas and the mass feed rate of said coal into said converting means for deriving said heating value, means for converting said coal into particulate form, gravimetric feeding means for feeding said coal at a constant mass rate and providing an output to said measuring means representing said mass feed rate of said coal, and means operated by pressurized air for transferring said coal from said feeding means to said converting means.

16. The system according to claim 15 wherein said converting means comprises a combustion chamber, means for initiation of the self-sustained combustion of said coal in said chamber, including means for preheating said chamber, and means controlling said feeding means for controlling the rate of delivery of said coal until said self-sustained combustion takes place.

17. The system according to claim 16 wherein said preheating means comprises a source of fuel gas, connected to said chamber, means for igniting said gas, and means for decreasing the flow of said gas while increasing the feed rate of said coal.

18. The system according to claim 15 wherein said gravimetric feeding means comprises a belt, a hopper disposed over said belt, means for controlling the flow of particulate coal into and out of said hopper, means for driving said belt and controlling the speed thereof, and means for measuring the weight of coal on said belt.

19. The system according to claim 18 wherein said hopper has a negative draft.

20. The system according to claim 18 wherein said hopper flow controlling means comprises means for sensing the level of coal in said hopper, and a dam at the exit end of said hopper moveable into and out of said exit end.

21. The system according to claim 20 further comprising pulverizer means for delivering said pulverized coal to said hopper, and means operative at a plurality of feed speeds for feeding said coal into said pulverizer.

22. The system according to claim 15 wherein said transferring means comprises a Venturi eductor having a hopper for receiving said coal from said gravimetric feeder.

23. The system according to claim 15 wherein said measuring means further comprises means for measuring the mass rate of total air flow which contributes to said combined gas including to said combustion gas.

* * * * *